United States Patent [19]
Maeda et al.

[11] Patent Number: 5,343,734
[45] Date of Patent: Sep. 6, 1994

[54] SAMPLING METHOD IN INFUSION PUMP APPARATUS

[75] Inventors: Akihiro Maeda, Kyoto, Japan; Thomas Callaghan, Algonquin, Ill.

[73] Assignees: Sharp Kabushiki Kaisha, Osaka, Japan; Baxter Int'l Inc., Deerfield, Ill.

[21] Appl. No.: 940,342

[22] Filed: Sep. 3, 1992

[30] Foreign Application Priority Data

Sep. 4, 1991 [JP] Japan ............................ 3-223935
Jul. 13, 1992 [JP] Japan ............................ 4-185033

[51] Int. Cl.$^5$ .......................................... G01N 7/00
[52] U.S. Cl. ................................ 73/19.01; 604/123
[58] Field of Search ............ 73/19.1, 19.01, 61.44, 73/61.48; 128/DIG. 13; 604/122, 123; 340/608, 632

[56] References Cited

U.S. PATENT DOCUMENTS

| | | | |
|---|---|---|---|
| 3,566,685 | 3/1971 | Zimmerman et al. | 73/61.44 |
| 4,255,088 | 3/1981 | Newton et al. | |
| 4,565,500 | 1/1986 | Jeensalute et al. | 604/123 |
| 4,919,650 | 4/1990 | Feingold et al. | 128/DIG. 13 |
| 4,981,467 | 1/1991 | Bobo, Jr. et al. | 604/122 |

Primary Examiner—Robert Raevis
Attorney, Agent, or Firm—Birch, Stewart, Kolasch & Birch

[57] ABSTRACT

A sampling method for sampling an output emerging from a bubble detector used in an infusion device of a type including an resilient infusion tubing, a peristaltic pump including a plurality of juxtaposed finger members for sequentially squeezing a portion of the infusion tubing while producing at least one moving zone of occlusion along the infusion tubing for infusing a medical solution intravenouly, a stepper motor for driving the peristaltic pump. The sampling of an output from the bubble detector is carried out only during a first period from the timing at which a most upstream member of the finger members squeezes that portion of the infusion tubing to the timing at which a most downstream member of the finger members closest to the destination subsequently squeezes that portion of the infusion tubing, but not during a second period from the timing at which the most downstream finger member squeezes that portion of the infusion tubing to the timing at which the most upstream finger member squeezes that portion of the infusion tubing.

4 Claims, 4 Drawing Sheets

Liveband

Deadband

SAMPLING METHOD IN INFUSION PUMP APPARATUS

BACKGROUND OF THE INVENTION

1. Field of the Invention

The present invention generally relates to an intravenous infusion of medical solutions to a patient and, more particularly, to a method of sampling an output signal generated from a bubble detector in a peristaltic I.V. infusion pump apparatus.

2. Description of the Prior Art

The I.V. infusion device now in wide use makes use of a bubble detector for detecting the presence of bubbles in a medical solution then flowing through an I.V. line leading to a patient, By sampling output signals emerging from the bubble detector, the size of a bubble present in the medical solution can be determined.

The I.V. infusion device generally includes a peristaltic infusion pump for the intravenous administration of a medical solution to a patient. An example of the prior art peristaltic infusion pump is generally shown by 60 in FIG. 7. As shown in FIG. 7, the prior art peristaltic infusion pump 60 comprises upper and lower support arms Ca and Cb spaced apart from each other to define a finger chamber therebetween, a drive shaft 62 rotatably supported by the upper and lower support arms Ca and Cb by means of suitable bearings, a plurality of, for example, eight, cam lobes 63a to 63h mounted eccentrically on the drive shaft 62 for rotation together therewith, and fingers 64a to 64h equal in number to the cam lobes 63a and 63h housed within the finger chamber of the casing C and adapted to be successively driven in a direction perpendicular to the drive shaft 82 during the rotation of the drive shaft 62.

Each fingers 64a to 64h has an aperture defined therein so as to receive a corresponding cam lobe 63a to 63h therein. The cam lobes 63a to 63b are rigidly mounted on the drive shaft 62 in a helical pattern along the drive shaft 62 so that, during each complete rotation of the drive shaft 62 in one direction driven by a suitable drive motor (not shown), the cam lobes 63a to 63h will successively drive the respective fingers 64a to 64b in a direction perpendicular to the drive shaft 62 with the fingers 64a to 64h consequently producing a peristaltic action to that portion of an elastic infusion tubing 61 which extends so as to traverse the finger chamber in a direction generally parallel to the drive shaft 62 and which is positioned between a backup plate 68 and respective finger tips of the fingers 64a to 64h. It is to be noted that the infusion tubing 61 has an upstream end communicated with a known source of medical solution to be intraveously infused and a downstream end communicated with a needle or catheter and then into a vascular system, for example, a vein, of a patient.

In general, the illustrated peristaltic infusion pump is so designed that, during each complete rotation of the drive shaft 62, the cam lobes 63a to 63h successively drive the associated fingers 64a to 64h to cause the latter to undergo a linear peristaltic motion with the finger tips consequently sequentially squeezing that portion of the infusion tubing 61 while producing at least one moving zone of occlusion along said infusion tubing, thereby to transport the medical solution successively towards the downstream end of the infusion tubing 61 and then towards the vascular system of the patient.

As is well known to those skilled in the art, the flow of the medical solution through that portion of the infusion tubing 61 takes place only during a period from the timing at which the finger tip of the uppermost or most upstream finger 64a squeezes the infusion tubing 61 in cooperation with the backup plate 68 to the timing at which the finger tip of the lowermost or most downstream finger 64h subsequently squeezes the infusion tubing 61 in cooperation with the backup plate 68.

On the other hand, no flow of the medical solution through that portion of the infusion tubing 61 takes place during a period from the timing at which the finger tip of the lowermost or most downstream finger 64h squeezes the infusion tubing 61 in cooperation with the backup plate 68 to the timing at which the finger tip of the uppermost or most upstream finger 64a subsequently squeezes the infusion tubing 61 in cooperation with the backup plate 68. This period is well known as a deadband, and this deadband occurs as a result of a difference in pressure between respective portions of the infusion tubing 61 upstream and downstream of the finger tip of the most downstream finger 64h then squeezing the infusion tubing 61.

It is to be noted that, for the purpose of the present invention, while the second mentioned period during which no flow of the medical solution take place is known as the deadband, the first mentioned period during which the flow of the medical solution takes place is referred to as a liveband.

According to the conventionally practiced sampling technique, the physical inherence of the deadband and the liveband in the sophisticated peristaltic infusion pump is not taken into consideration, and an output signal emerging from a bubble detector is generally sampled at a predetermined uniform interval by the use of a timer over the entire sampling period. This means that, even during the deadband period, the output signal emerging from the bubble detector is sampled for the detection of the presence or absence of a bubble in the infusion tubing.

Considering that no flow of the medical solution through the infusion tubing take place during the deadband, no change take place in the output of the bubble detector and, therefore, the sampling of the output signal emerging from the bubble detector has no significance and is nothing other than the futility. Also, the sampling of the detector output during the deadband period tends to adversely affect the algorith, used to detect the presence of the bubble in the medical solution within the infusion tubing, to such an extent as to result in a variation in size of bubbles detected by the bubble detector. By way of example, assuming that the algorith is employed of a kind designed to detect bubbles of a predetermined size in reference to the length of time over which the bubble intercepts the bubble detector, and if the deadband starts at the moment the bubble comes to a position intercepting the bubble detector as shown in FIG. 5(a), the bubble remains intercepting the bubble detector throughout the deadband period. Therefore, if the sampling continues even during the deadband, the detector output indicative of the presence of the bubble will have a duration longer than that generated from the bubble detector during the flow of the medical solution taking place, that is, during the liveband, and therefore the bubble detector will be apt to detect bubbles of a size smaller than the bubble size desired to be detected.

SUMMARY OF THE INVENTION

The present invention has for its object to provide an improved sampling method for sampling an output from a bubble detector wherein the sampling is carried out only during the liveband period and will not take place during the deadband period, thereby to avoid the futility of the sampling and which is effective to ensure a detection of bubbles with no variation in size of bubbles detected by the bubble detector.

To this end, the present invention provides a sampling method for sampling an output emerging from a bubble detector used in an infusion device of a type comprising an resilient infusion tubing communicated at an upstream end thereof with a source of medical solution and at a downstream end thereof with a destination, a peristaltic means including a plurality of juxtaposed finger members adapted to be sequentially driven to operatively engage a portion of the infusion tubing to sequentially squeeze said portion of the infusion tubing while producing at least one moving zone of occlusion along said infusion tubing for infusing a medical solution from the source of the medical solution towards the destination, a drive means for driving the peristaltic means to sequentially drive the finger members.

In accordance with the present invention, the sampling of the output from the bubble detector is carried out only during a first period from the timing at which one of the finger members closest to the source of the medical solution squeezes that portion of the infusion tubing to the timing at which one of the finger members closest to the destination squeezes that portion of the infusion tubing, and is not carried out during a second period from the timing at which one of the finger members closest to the destination squeezes that portion of the infusion tubing to the timing at which one of the finger members squeezes that portion of the infusion tubing.

Preferably, the drive means may comprise a stepper motor, a drive shaft drivingly coupled with the stepper motor and a cam lobe for each of the finger members. The respective cam lobe is mounted on the drive shaft for rotation together therewith for translating a rotary motion of the drive shaft into a linear movement performed by the associated finger member. In this system, the first and second periods are preferably determined in dependence on the number of pulses used to drive the stepper motor.

The drive means may also comprise a rotary disc mounted on the drive shaft for rotation together therewith and having a peripheral portion formed with a plurality of circumferentially spaced slits. In this case, the use may be made of a sensor unit for detecting the angle of rotation of the rotary disc in terms of the number of the slits which have passed across the sensor unit, so that the first and second periods can be determined in dependence on the number of the slits detected by the sensor unit as having passed across the sensor unit.

BRIEF DESCRIPTION OF THE DRAWINGS

This and other objects and features of the present invention will become clear from the following description taken in conjunction with a preferred embodiment thereof with reference to the accompanying drawings, in which like parts are designated by like reference numerals and in which.

DETAILED DESCRIPTION OF THE PREFERRED EMBODIMENT

Figure 1:
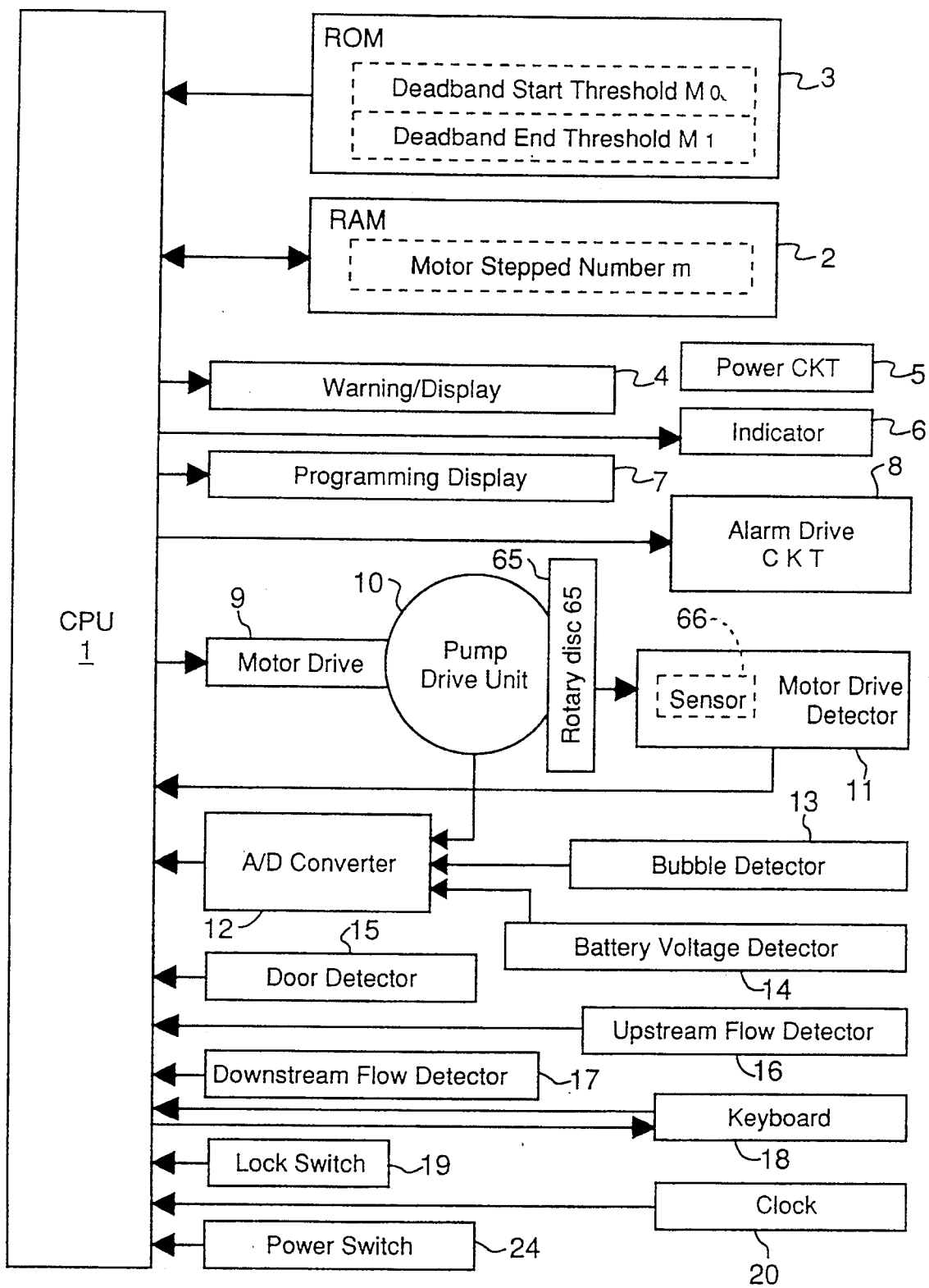
FIG. 1 is a block diagram showing an intravenous infusion pump apparatus employing a sampling method of the present invention.

Referring first to FIG. 1, an intravenous infusion pump apparatus embodying the present invention comprises a central processing unit (CPU) 1, a random access memory (RAM) 2, and a read-only memory (ROM) 8. The central processing unit 1 supervises the entire sequence of operation of the infusion pump apparatus as a whole whereas the random access memory 2 is used for a temporary storage of various data used in arithmetic calculations performed by the central processing unit 1. The read-only memory 8 stores a program necessary to operate the central processing unit 1. A warning/display indicator 4 is adapted to receive signals, detected by various detectors as will be described later, through the central processing unit to provide an audible and/or visual message represented by such signals.

An electric power supply circuit 5 provides all necessary electric power to various circuit components of the apparatus. An indicator lamp 8 is operable to provide an indication that the apparatus is issuing an audible and-/or visual warning during the administration of a medical solution to a patient through a peristaltic infusion pump assembly as will be described later. A programming display 7 is operable to provide a display of information associated with the infusion of the medical solution such as, for example, the flow rate of the medical solution being administrated, the total amount of the medical solution to be administrated and the cumulative amount of the medical solution administrated. An alarm drive circuit 8 is operable, when the apparatus is in a state of emergency, to drive an alarm to call an attention of an attendant physician or nurse. A pump drive unit 10 includes an electrically driven stepper motor for driving the peristaltic infusion pump assembly 60 shown in FIG. 2. A motor drive circuit 9 is used to drive the stepper motor in response to a series of drive pulses outputted from the central processing unit 1.

A motor drive detector 11 is used to detect, and provides to the central processing unit 1 a motor drive signal indicative of, the number of revolutions of the stepper motor. It is to be noted that the number of revolutions of the stepper motor detected by this motor drive detector 11 corresponds to the amount of the medical solution being delivered to the patient through the peristaltic infusion pump assembly.

A bubble detector 13 is used to detect the presence or absence of bubbles in the infusion tubing 61. An analog-to-digital (A/D) converter 12 is operable to convert analog signals indicative of the level of detection of bubbles and the level of a battery voltage into respective digital signals which are in turn supplied to the central processing unit 1. A door detector circuit 15 monitors a door of the apparatus and provides a door open signal when the door is opened.

An upstream flow detector circuit 16 is used to detect a reduction in pressure inside an upstream portion of the infusion tubing 61 between a solution bag (the source of the medical solution) and the peristaltic infusion pump assembly 60 which would take place as a result of an occurrence of an abnormality, for example, a clogging, in that upstream portion of the infusion tubing 61. A downstream flow detector circuit 17 is operable to detect an increase in pressure inside a downstream portion of the infusion tubing 61 between the peristaltic infusion pump assembly 60 and the patient which would take place as a result of an occurrence of an abnormality, for example, an occlusion, in that downstream portion of the infusion tubing 61.

A keyboard 18 adapted to be manipulated by an operator of the apparatus when the apparatus is desired to be operated includes a plurality of numerical input keys through which an operator of the apparatus can input the amount of the medical solution to be administrated and the flow rate thereof, a plurality of control keys for assisting the inputting, a START key for initiating the administration of the medical solution when depressed, a STOP key for interrupting the administration of the medical solution when depressed, a CALL key for causing the cumulative amount of the medical solution administrated when depressed. A lock switch 19 is used to lock the keyboard 18 and an electric power supply key in a disabled condition for the purpose of avoiding the possibility that the apparatus may be manipulated by those other than the authorized operator, i.e., the authorized attendant physician or nurse.

A clock 20 is used to provide visual information on the length of time during which the apparatus is operated and the time at which any warning is made and for any other purpose. An electric power switch 24 is used to selectively switch the power supply circuit 5 on and off.

For the purpose of the present invention, the random access memory 2 referred to above stores the motor stepped number m, i.e., the number of counted steps over which the stepper motor are rotated or advanced, which may be equal to or a function of the number of motor drive pulses outputted from the central processing unit 1 to the motor drive circuit 9. On the other hand, the read-only memory 3 stores a first threshold value $M_0$, descriptive of the start of the deadband, and a second threshold value $M_1$ descriptive of the termination of the deadband. Each of the first and second threshold values $M_0$ and $M_1$ may be represented by the different number of steps to which the stepper motor has been driven stepwise.

Figure 2:
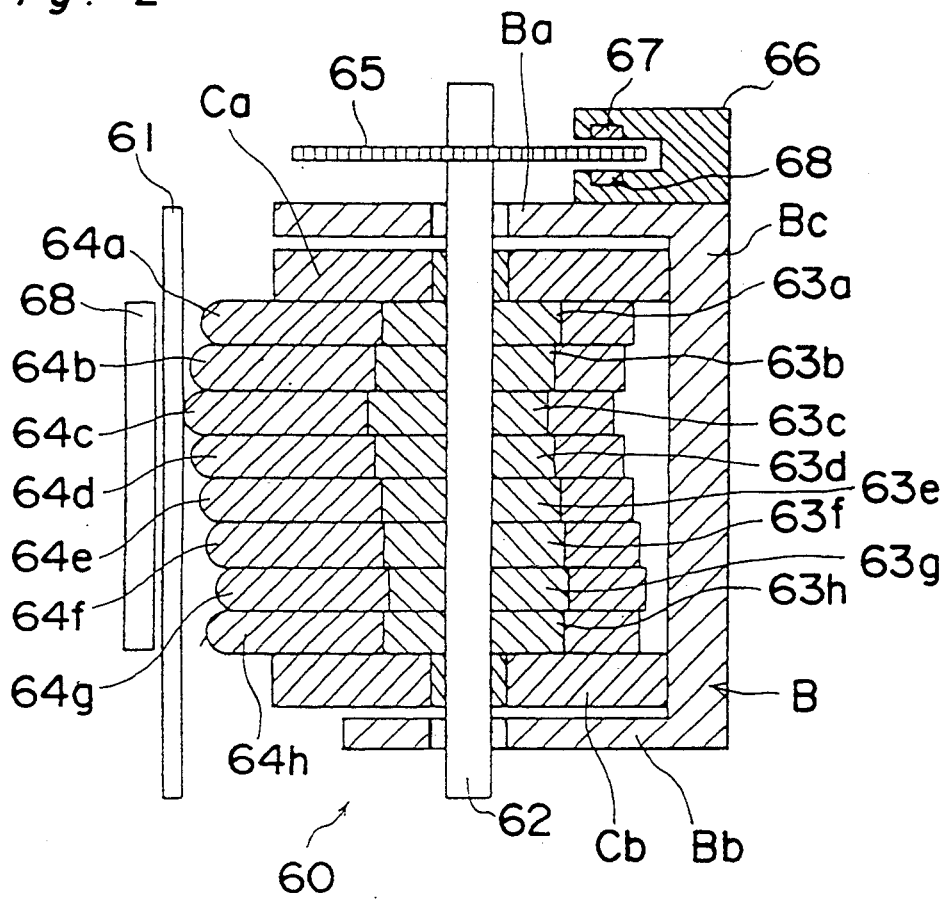
FIG. 2 is a schematic side sectional view, on an enlarged scale, showing a peristaltic infusion pump assembly used in the practice of the present invention.
Figure 7:
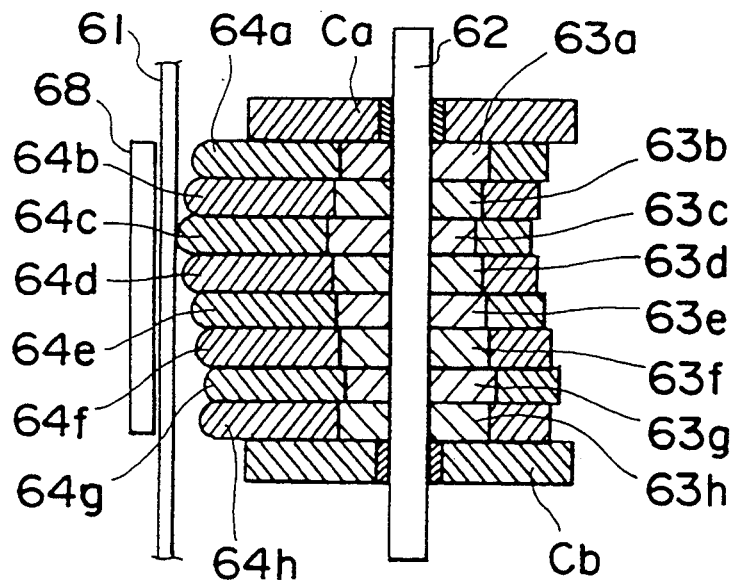
FIG. 7 is a side sectional view of the prior art peristaltic infusion pump.

Referring now to FIG. 2 for the discussion of the details of the peristaltic infusion pump assembly 60, the pump assembly 60 shown therein is generally similar to that shown in and discussed with reference to FIG. 7 in that the both include the plurality of the cam lobes 63a to 63h rigid on the drive shaft 62 and the plurality of the fingers 64a to 64h operatively positioned between the arms Ca and Cb and adapted to be sequentially driven in the direction perpendicular to the drive shaft 62 between retracted and projected positions to form a moving zone of occlusion along the infusion tubing 61 in cooperation with the backup plate 68. However, the peristaltic pump assembly 60 shown in FIG. 2 differs from that shown in FIG. 7 in that, for mounting of a sensor unit as will be described later, a generally C-shaped bracket B of one-piece construction having upper and lower bracket arms Ba and Bb and a bridge Bc connecting the bracket arms Ba and Bb together is employed while the support arms Ca and Cb are rigidly secured to, or otherwise formed integrally with, the bridge Bc of the C-shaped bracket B so as to extend parallel to the adjacent bracket arms Ba and Bb. It is to be noted that, if the bracket arms Ba and Bb are so designed as to have respective bearings for the support of the drive shaft 62 and the space between the bracket arms Ba and Bb is chosen to be of a size sufficient to operatively accommodate the fingers 64a to 64h together with the cam lobes 63a to 63h, the use of the upper and lower support arms Ca and Cb may be dispensed with.

In any event, the peristaltic infusion pump assembly of the construction so far described is well known and, therefore, no further detail thereof will be reiterated for the sake of brevity.

Figure 3:
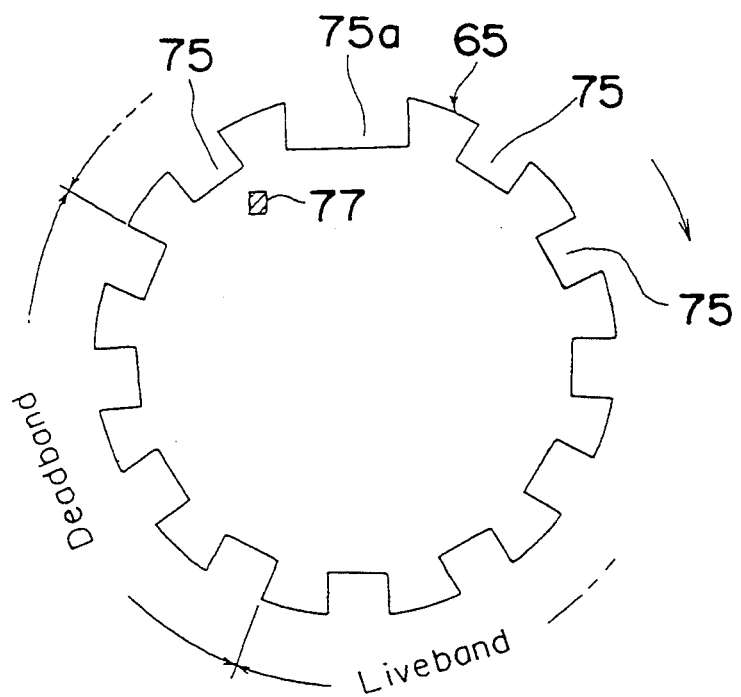
FIG. 3 is a top plan view of an encoder rotary disc, on a further enlarged scale, employed in the peristaltic pump assembly shown in FIG. 2.

Rigidly mounted on the drive shaft 62 and positioned on one side of the bracket arm Ba remote from the stack of the fingers 64a to 64h is a rotary disc 65 supported for rotation together with the drive shaft 62. As best shown in FIG. 3, the rotary disc 65 has its outer peripheral portion formed with a plurality of, for example, twelve, slits 75 that are circumferentially equally spaced from each other about the axis of rotation thereof, i.e., the drive shaft 62, one of said slits 75 being, as indicated by 75a, of a width greater than that of any one of the remaining slits 75. This rotary disc 65 also has a reference slit 77 defined therein in the form of an aperture at a location radially inwardly of one of the slits 75 which is positioned on a trailing side of the larger width slit 75a with respect to the direction thereof as indicated by the arrow. This reference slit 77 is utilized to define a reference position of the rotary disc 65.

The sensor unit 66 mounted atop the bracket arm Ba as shown in FIG. 2 forms a part of the motor drive detector 11 shown in FIG. 1 and includes a generally C-shaped casing having a pair of spaced arms carrying a light emitting element 67 and a light receiving element 68, respectively. The light emitting element 67 and the light receiving element 68 are positioned and supported in face-to-face relationship with each other on respective sides of the path of movement of the slits in the rotary disc 65. Thus, it will readily be seen that, during each complete rotation of the rotary disc 65 together with the drive shaft 62, the sensor unit 66 detects a passage of rays of light from the light emitting element 67 towards the light receiving element 68 through the slits 75 and 75a and 77 and provides the central processing unit 1 with a signal indicative of the passage of the rays of light through the slits. In FIG. 3, of the twelve slits 75 and 75a, the successive four slits 75 are shown as corresponding to the deadband while the remaining slits 75 and 75a are shown as corresponding to the liveband.

The central processing unit 1 shown in FIG. 1 applies a pulse signal through the motor drive circuit 9 to the pump drive unit 10 to drive the stepper motor. As the stepper motor is so driven, the drive shaft 62 shown in FIG. 2 is driven in one direction about its own longitudinal axis thereby sequentially driving the fingers 64a to 64h in the manner as hereinbefore discussed to deliver the medical solution through that portion of the infusion tubing 61. As is well known to those skilled in the art, during the rotation of the drive shaft 62 in one direction, the liveband and the deadband repeatedly alternate each other. The motor drive detector 11 outputs an interruption signal to the central processing unit 1 when rotary disc 65 being rotated together with the drive shaft 62 comes to a predetermined position, that is, when the sensor unit 66 detects the passage of light through the reference slit 77 in the rotary disc 65. The central processing unit 1 then refers to the number of pulses outputted to the pump drive unit 10 to determine whether the liveband is in progress or whether the deadband is in progress. Once the liveband is determined in progress, the central processing unit executes a sampling of an output signal from the bubble detector 13 cyclically at predetermined equal intervals to detect the presence of a bubble of a size greater than a predetermined bubble size.

Figure 5A:
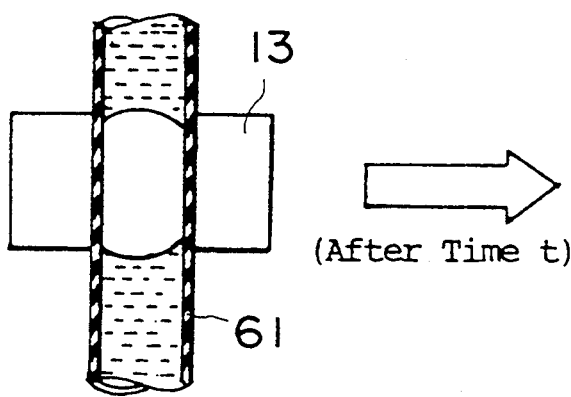
FIGS. 5(a) and 5(b) are explanatory diagrams showing how a bubble in the infusion tubing is detected during a deadband period.
Figure 5B:
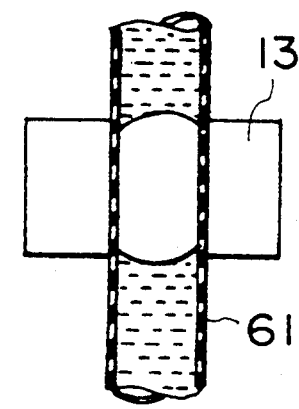

FIGS. 5(a) and 5(b) illustrate a condition in which the deadband period starts when the bubble in the infusion tubing 61 comes to a position intercepting the bubble detector 13 and a condition in which the bubble remains in position to intercept the bubble detector 13 after the subsequent passage of a predetermined time t while the deadband is in progress, respectively. Accordingly, if the sampling of the output signal from the bubble detector 13 is continued during this deadband period, there is the possibility that the presence of bubbles of a size not greater than the predetermined bubble size may be detected.

Figure 4A:
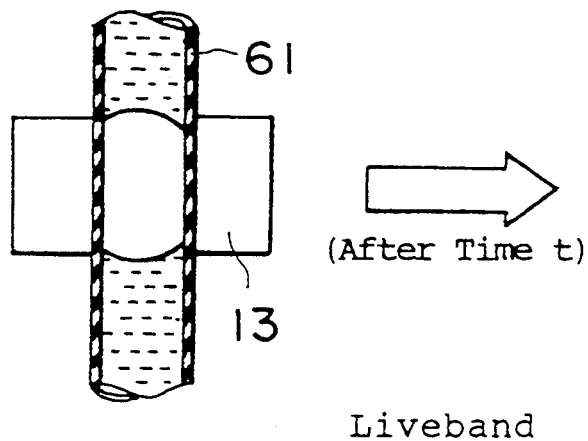
FIGS. 4(a) and 4(b) are explanatory diagrams showing how a bubble in an infusion tubing is detected during a liveband period.
Figure 4B:
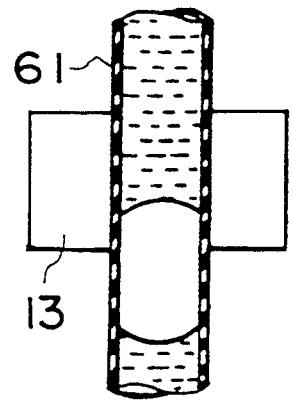

FIGS. 4(a) and 4(b) illustrates the passage of the bubble through the infusion tubing 61 across the bubble detector 13 after the predetermined time t while the liveband is in progress. By sampling the output signal generated from the bubble detector 13 during the liveband period, the presence of the bubble of a size greater than the predetermined bubble size can be accurately detected.

Figure 6A:
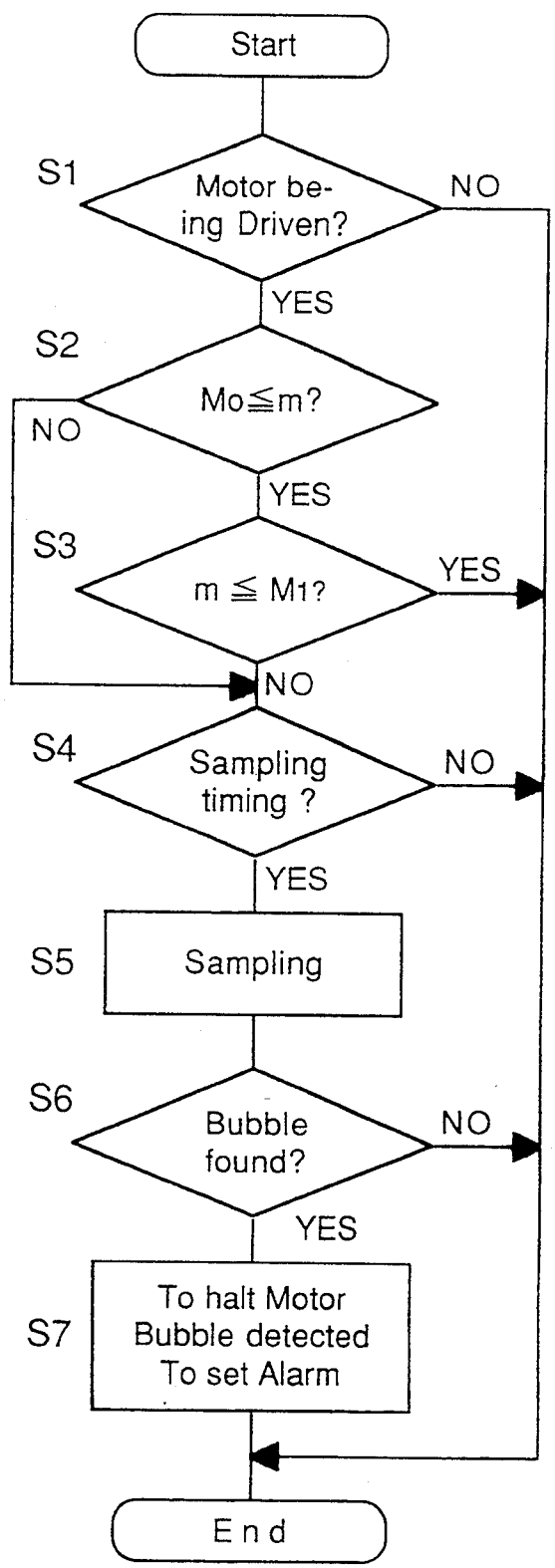
FIGS. 6(a) to 6(c) are flowcharts showing the sequence of sampling according to the present invention.

The sequence of sampling performed by the central processing unit 1 will now be described with reference to the flowcharts shown in FIGS. 6(a) to 6(c).

Figure 6B:
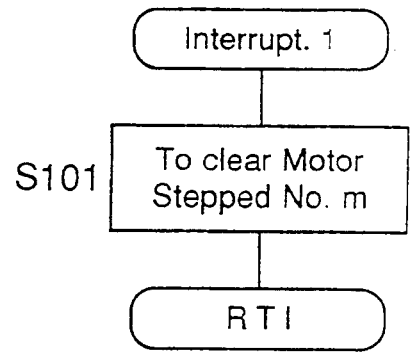
Figure 6C:
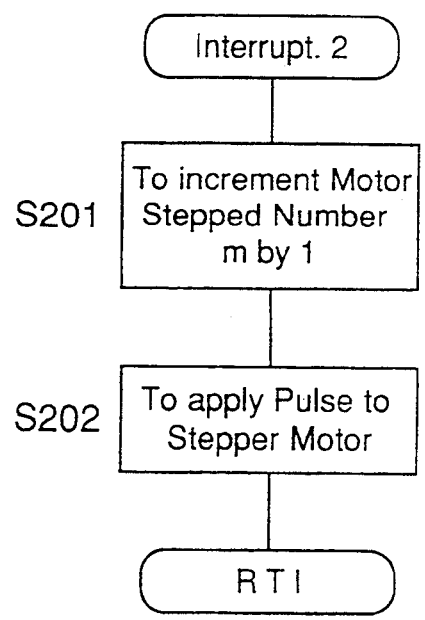

When the interruption signal is applied from the motor drive detector 11 to the central processing unit 1, the latter executes an interruption flow shown in FIG. 6(b). By this interruption flow of FIG. 6(b), the motor stepped number m stored in the random access memory 2 is initialized (i.e., cleared) to zero at step S101. This central processing unit 1 also executes another interruption flow shown in FIG. 6(c) when the timing comes at which the pulse is to be outputted to the motor drive circuit 9. By this interruption flow of FIG. 6(c), the motor stepped number m stored in the random access memory 2 is incremented by one at step S201, followed by step S202 at which the output pulse from the central processing unit 1 is applied to the motor drive circuit 9.

The central processing unit 1 makes a decision at step S1 to determine if the stepper motor is being rotated. If a result of decision at step S1 indicates that the stepper motor is being rotated, the program flow goes to step S2 at which another decision is made to determine if the motor stepped number m is equal to or greater than the first threshold value $M_0$ stored in the read-only memory 3. If a result of decision at step S2 indicates that the motor stepped number m is smaller than the threshold value $M_0$ signifying that the stepper motor is being driven during the liveband period, the program flow goes to step S4.

On the other hand, if the result of decision at step S2 indicates that the motor stepped number m is equal to or greater than the threshold value $M_0$ signifying that the stepper motor is being driven during the deadband period, the program flow goes to a further decision step S3 at which a decision is made to determine if the motor stepped number m is equal to or smaller than the second threshold value $M_1$ stored in the read-only memory 3. If a result of decision at step S3 indicates that the motor stepped number m is equal to or smaller than the second threshold value signifying that the stepper motor is being driven during the deadband period, the program flow terminates with no sampling of the output signal from the bubble detector 13 being carried out.

On the other hand, if the result of decision at step S3 indicates that the motor stepped number m is greater than the second threshold value $M_1$ signifying that the stepper motor is being driven during the liveband period, the program flow goes to step S4 at which a decision is made to determine if the time has come to perform the sampling of the output signal from the bubble detector 13. If a result of decision at step S4 indicates that it is not the timing for the execution of the sampling, the program flow terminates, but if the result of decision at step S4 indicates that it is the timing for the execution of the sampling, the sampling is performed by the central processing unit 1 at step S5 to detect the presence or absence of a bubble in the infusion tubing 61, followed by step S6 at which a decision is made to determine if the infusion tubing 61 contains the bubble.

In the event that a result of decision at step S6 indicates that the infusion tubing 61 contains the bubble, the program flow goes to step S7 at which not only is the stepper motor brought to a halt, but the warning/display indicator 4, the indicator lamp 6 and the alarm drive circuit 8 are also energized to call the attention of the attendant physician or nurse that the infusion tubing 61 contains the bubble. On the other hand, if the result of decision at step S6 indicates that no bubble is found in the infusion tubing 61, the program flow terminates immediately.

As hereinabove described, the central processing unit 1 refers to the motor stepped number to determine whether the liveband is in progress or whether the deadband is in progress and executes the sampling of the output signal from the bubble detector 13 only during the liveband period to detect the presence in the infusion tubing 61 of the bubble of a size greater than the predetermined bubble size. Therefore, an unnecessary sampling of the output signal from the bubble detector does not take place and, also, no variation occurs in size of the bubble detected by the bubble detector.

From the foregoing description of the preferred embodiment of the present invention, it is clear that the sampling of the output from the bubble detector is carried out only during a first period from the timing at which one of the finger members closest to the source of the medical solution squeezes that portion of the infusion tubing to the timing at which one of the finger members closest to the destination squeezes that portion of the infusion tubing, and is not carried out during a second period from the timing at which one of the finger members closest to the destination squeezes that portion of the infusion tubing to the timing at which one of the finger members squeezes that portion of the infusion tubing. Therefore, only during a period in which the medical solution actually flows through the infusion tubing, the output signal generated from the bubble detector is sampled. This ensures an elimination of an unnecessary sampling of the output signal from the bubble detector and, also, that of any possible variation occurring in size of the bubble detected by the bubble detector.

Also, the drive means may comprise a stepper motor, a drive shaft drivingly coupled with the stepper motor and a cam lobe for each of the finger members. The respective cam lobe is mounted on the drive shaft for rotation together therewith for translating a rotary motion of the drive shaft into a linear movement performed by the associated finger member. In this system, the first and second periods can easily be determined in dependence on the number of pulses used to drive the stepper motor.

Furthermore, the drive means may also comprise a rotary disc mounted on the drive shaft for rotation together therewith and having a peripheral portion formed with a plurality of circumferentially spaced slits. In this case, the use may be made of a sensor unit for detecting the angle of rotation of the rotary disc in terms of the number of the slits which have passed across the sensor unit, so that the first and second periods can easily be determined in dependence on the number of the slits detected by the sensor unit as having passed across the sensor unit.

Although the present invention has fully been described in connection with the various embodiments thereof with reference to the accompanying drawings, it is to be noted that various changes and modifications are apparent to those skilled in the art. By way of example, although in the foregoing embodiment the use has been made of the first and second threshold values $M_0$ and $M_1$ which are stored in the read-only memory 3 and with which the motor stepped number m outputted from the central processing unit 1 is compared to determine the liveband and the deadband, the present invention may not be limited thereto and arrangement may be made to determine the liveband and the deadband by comparing the number of the slits 75 and 75a which pass across the sensor unit 66 with the first and second threshold values $M_0$ and $M_1$.

Also, while it has been described that the presence of the bubble of a size greater than the predetermined bubble size is detected by the sampling performed by the central processing unit 13 of the output signal from the bubble detector 13, it is possible to count the number of bubbles of a size greater than the predetermined bubble size that are found per unitary time.

Accordingly, such changes and modifications are to be understood as included within the scope of the present invention as defined by the appended claims, unless they depart therefrom.

What is claimed is:

1. A sampling method for sampling an output emerging from a bubble detector used in an infusion device of a type comprising an resilient infusion tubing communicated at an upstream end thereof with a source of medical solution and at a downstream end thereof with a destination, a peristaltic means including a plurality of juxtaposed finger members adapted to be sequentially driven to operatively engage a portion of the infusion tubing to sequentially squeeze said portion of the infusion tubing while producing at least one moving zone of occlusion along said infusion tubing for infusing a medical solution from the source of the medical solution towards the destination, a drive means for driving the peristaltic means to sequentially drive the finger members, said sampling of the output from the bubble detector being carried out only during a first period from the timing at which one of the finger members closer to the source of the medical solution squeezes that portion of the infusion tubing to the timing at which one of the finger members closer to the destination squeezes that portion of the infusion tubing, but not during a second period from the timing at which one of the finger members closer to the destination squeezes that portion of the infusion tubing to the timing at which one of the finger members closer to the source squeezes that portion of the infusion tubing.

2. The sampling method as claimed in claim 1, wherein said drive means comprise a stepper motor, a drive shaft drivingly coupled with the stepper motor and a cam lobe for each of the finger members, said cam lobe being mounted on the drive shaft for rotation together therewith for translating a rotary motion of the drive shaft into a linear movement performed by the associated finger member, and wherein the first and second periods are preferably determined in dependence on the number of pulses used to drive the stepper motor.

3. The sampling method as claimed in claim 1, further comprising a sensor unit, and wherein said drive means comprise a stepper motor, a drive shaft drivingly coupled with the stepper motor, a cam lobe for each of the finger members, said cam lobe being mounted on the drive shaft for rotation together therewith for translating a rotary motion of the drive shaft into a linear movement performed by the associated finger member, and a rotary disc mounted on the drive shaft for rotation together therewith and having a peripheral portion formed with a plurality of circumferentially spaced slits, said sensor unit being operable to detect the angle of rotation of the rotary disc in terms of the number of the slits which have passed across the sensor unit, and wherein the first and second periods are determined in dependence on the number of the slits detected by the sensor unit as having passed across the sensor unit.

4. A sampling method for sampling an output emerging from a bubble detector used in an infusion device of a type comprising a resilient infusion tubing communicated at an upstream end thereof with a source of medical solution and at a downstream end thereof with a destination, a peristaltic means, including a liveband region and a deadband region, for infusing a medical solution from the source of the medical solution towards the destination, a drive means for driving the peristaltic means, said method for sampling including the steps of:

determining whether the peristaltic means is in a liveband or deadband region, and sampling the output from the bubble detector only if the peristaltic means is in a liveband region.

* * * * *